(12) United States Patent
Crowley et al.

(10) Patent No.: US 8,150,521 B2
(45) Date of Patent: Apr. 3, 2012

(54) METHODS AND DEVICES FOR CONTROLLING BATTERY LIFE IN AN IMPLANTABLE PULSE GENERATOR

(75) Inventors: Thomas Patrick Crowley, Lino Lakes, MN (US); Jeffrey J. Hagen, Plymouth, MN (US)

(73) Assignee: CVRx, Inc., Minneapolis, MN (US)

( * ) Notice: Subject to any disclaimer, the term of this patent is extended or adjusted under 35 U.S.C. 154(b) by 955 days.

(21) Appl. No.: 12/049,956

(22) Filed: Mar. 17, 2008

(65) Prior Publication Data

US 2009/0018607 A1    Jan. 15, 2009

Related U.S. Application Data

(60) Provisional application No. 60/894,957, filed on Mar. 15, 2007, provisional application No. 60/951,114, filed on Jul. 20, 2007.

(51) Int. Cl.
*A61N 1/32* (2006.01)
(52) U.S. Cl. .......................................................... 607/44
(58) Field of Classification Search .................... 607/44, 607/18, 2
See application file for complete search history.

(56) References Cited

U.S. PATENT DOCUMENTS

| | | | |
|---|---|---|---|
| 4,556,061 A | 12/1985 | Barreras et al. |
| 4,715,381 A | 12/1987 | Moberg |
| 4,987,897 A | 1/1991 | Funke |
| 5,113,859 A | 5/1992 | Funke |
| 5,331,966 A | 7/1994 | Bennett et al. |
| 5,344,431 A | 9/1994 | Merritt et al. |
| 5,402,070 A | 3/1995 | Shelton et al. |
| 5,458,624 A | 10/1995 | Renirie et al. |
| 5,700,282 A | 12/1997 | Zabara |
| 5,741,307 A | 4/1998 | Kroll |
| 5,769,873 A | 6/1998 | Zadeh |
| 5,810,735 A | 9/1998 | Halperin et al. |
| 5,904,708 A | 5/1999 | Goedeke |
| 5,987,352 A | 11/1999 | Klein et al. |
| 6,073,048 A | 6/2000 | Kieval et al. |
| 6,106,477 A | 8/2000 | Miesel et al. |
| 6,108,579 A | 8/2000 | Snell et al. |
| 6,178,349 B1 | 1/2001 | Kieval |
| 6,185,461 B1 | 2/2001 | Er |
| 6,292,695 B1 | 9/2001 | Webster, Jr. et al. |

(Continued)

FOREIGN PATENT DOCUMENTS

WO    WO 98/02209    1/1998

(Continued)

OTHER PUBLICATIONS

Coleridge et al., "Impulse in Slowly Conducting Vagal Fibers from Afferent Endings in the Veins, Atria, and Arteries of Dogs and Cats," Circ. Res. (1973) 23:87-97.

(Continued)

*Primary Examiner* — Carl H. Layno
*Assistant Examiner* — Jon-Eric C. Morales
(74) *Attorney, Agent, or Firm* — Patterson Thuente Christensen Pedersen, P.A.

(57) ABSTRACT

Methods, devices, and systems for controlling an implantable pulse generator for activation of a nerve or receptor are provided. In particular, the method, devices, and systems embodying features of the present invention control the energy output of a battery in an implantable pulse generator for stimulation of the baroreflex system of the patient.

3 Claims, 5 Drawing Sheets

U.S. PATENT DOCUMENTS

| | | |
|---|---|---|
| 6,400,988 B1 | 6/2002 | Gurewitsch |
| 6,498,950 B1 * | 12/2002 | Bradley .......................... 607/27 |
| 6,522,926 B1 | 2/2003 | Kieval et al. |
| 6,584,355 B2 | 6/2003 | Stessman |
| 6,616,624 B1 | 9/2003 | Kieval |
| 6,654,640 B2 | 11/2003 | Lyden |
| 6,666,826 B2 | 12/2003 | Salo et al. |
| 6,671,552 B2 | 12/2003 | Merrit et al. |
| 6,701,186 B2 | 3/2004 | Spinelli et al. |
| 6,704,598 B2 | 3/2004 | Ding et al. |
| 6,748,272 B2 | 6/2004 | Carlson et al. |
| 6,766,189 B2 | 7/2004 | Yu et al. |
| 6,768,923 B2 | 7/2004 | Ding et al. |
| 6,820,019 B1 | 11/2004 | Kelly et al. |
| 6,850,801 B2 | 2/2005 | Kieval et al. |
| 6,901,293 B2 | 5/2005 | Rogers et al. |
| 6,985,774 B2 | 1/2006 | Kieval et al. |
| 7,158,832 B2 | 1/2007 | Kieval et al. |
| 7,848,812 B2 | 12/2010 | Crowley et al. |
| 2003/0060858 A1 * | 3/2003 | Kieval et al. ..................... 607/44 |
| 2003/0171791 A1 | 9/2003 | Kenknight et al. |
| 2003/0199806 A1 | 10/2003 | Kieval |
| 2004/0010303 A1 | 1/2004 | Bolea et al. |
| 2004/0019364 A1 | 1/2004 | Kieval et al. |
| 2004/0254616 A1 | 12/2004 | Rossing et al. |
| 2005/0102005 A1 | 5/2005 | Krig et al. |
| 2005/0177206 A1 | 8/2005 | North et al. |
| 2006/0004417 A1 | 1/2006 | Rossing et al. |
| 2006/0025829 A1 | 2/2006 | Armstrong et al. |
| 2006/0074453 A1 | 4/2006 | Kieval et al. |
| 2007/0156198 A1 | 7/2007 | Rossing et al. |
| 2007/0179547 A1 | 8/2007 | Armstrong et al. |
| 2008/0167696 A1 | 7/2008 | Cates et al. |

FOREIGN PATENT DOCUMENTS

| | | |
|---|---|---|
| WO | WO 99/51286 A1 | 10/1999 |
| WO | WO 00/16686 | 3/2000 |
| WO | WO 02/26314 | 4/2002 |
| WO | WO 2008/083235 | 7/2008 |

OTHER PUBLICATIONS

Goldberger et al., "New Technique for Vagal Nerve Stimulation," J. Neuro. Meth. (1999) 91:109-114.

Kostreva et al., "Hepatic Vein, Hepatic Parenchymal, and Inferior Vena Caval Mechanoreceptors with Phrenic Afferents," Am. J. Physiol. (1993) 265:G15-G20.

Mifflin et al., "Rapid Resetting of Low Pressure Vagal Receptors in the Superior Vena Cava of the Rat," Circ. Res. (1982) 51:241-249.

Rau et al., "Psychophysiology of Arterial Baroreceptors and the Etiology of Hypertension," Biol. Psychol. (2001) 57:179-201.

Schauerte et al., "Transvenous Parasympathetic Nerve Stimulation in the Inferior Vena Cava and Atrioventricular Conduction," J. Cardiovasc. Electrophysiol. (2000) 11:64-69.

U.S. Appl. No. 60/584,730, filed Jun. 30, 2004; Inventor: Martin Rossing.

U.S. Appl. No. 60/894,957, filed Mar. 13, 2007; Inventor: Thomas Crowley.

U.S. Appl. No. 10/284,063, filed Oct. 29, 2002; Inventor: Robert Kieval.

International Search Report, PCT/US2008/070641, dated Jan. 29, 2009. 2 pages.

International Preliminary Report on Patentability, PCT/US2008/070641, dated Jan. 26, 2010. 6 pages.

* cited by examiner

METHODS AND DEVICES FOR CONTROLLING BATTERY LIFE IN AN IMPLANTABLE PULSE GENERATOR

CROSS-REFERENCES TO RELATED APPLICATIONS

This application claims the benefit of U.S. Provisional Application Nos. 60/894,957, filed Mar. 15, 2007, and 60/951,114, filed Jul. 20, 2007, the disclosures of which are each incorporated herein by reference in their entireties. This application is related to, but does not claim the benefit of the following U.S. Patents and Applications, all of which are fully incorporated herein by reference in their entirety: U.S. Pat. Nos. 6,522,926; 6,616,624; 6,985,774; 7,158,832; 6,850,801; PCT Patent Application No. PCT/US01/30249, filed Sep. 27, 2001; U.S. patent application Ser. Nos.: 10/284,063, filed Oct. 29, 2002; 10/453,678, filed Jun. 2, 2003; 10/402,911, filed Mar. 27, 2003; 10/402,393, filed Mar. 27, 2003; 10/818,738, filed Apr. 5, 2004; 60/584,730, filed Jun. 30, 2004; 11/168,231, filed Jun. 27, 2005; 10/958,694, filed Oct. 4, 2004; and 60/882,478, filed Dec. 28, 2006; and 60/883,721, filed Jan. 5, 2007.

BACKGROUND OF THE INVENTION

1. Field of Invention

The present invention relates generally to medical devices and methods of use for the treatment and/or management of cardiovascular, neurological, and renal disorders, and more specifically to devices and methods for controlling the energy consumption of a battery in an implantable pulse generator of baroreflex systems for the treatment and/or management of cardiovascular, neurological, and renal disorders and their underlying causes and conditions.

Implantable pulse generator medical devices are well known in the art, and include medical devices. Generally, these medical devices comprise an implantable pulse generator unit including a battery as the source of energy. A problem associated with pulse generators (e.g., implantable or external) is battery depletion. Such problems include: loss of therapy, which in some cases may be life-sustaining; rebound or similar disadvantageous effects if the therapy were abruptly discontinued (as for example in the case of pulse generators for use in regulating blood pressure, abrupt cessation of therapy may result in the blood pressure to revert to levels higher than even that of pre-therapy baseline. Hence, such abrupt cessation needs to be avoided, thus there is the advantage of avoiding loss of battery, or at least reducing therapy gradually before battery depletion). Furthermore, another problem is the loss of data stored in volatile memory in the device. Thus, it would be important to avoid abrupt cessation of therapy due to loss of battery, or at least reducing the therapy gradually before the depletion of the battery. Furthermore, such abrupt cessation may also result in loss of data stored in the volatile memory in the device.

Hypertension, or high blood pressure, is a major cardiovascular disorder that is estimated to affect 65 million people in the United States alone, and is a leading cause of heart failure and stroke. It is listed as a primary or contributing cause of death in over 200,000 patients per year in the United States alone. Hypertension occurs in part when the body's smaller blood vessels (arterioles) constrict, causing an increase in blood pressure. Because the blood vessels constrict, the heart must work harder to maintain blood flow at the higher pressures. Sustained hypertension may eventually result in damage to multiple body organs, including the kidneys, brain, eyes and other tissues, causing a variety of maladies associated therewith. The elevated blood pressure may also damage the lining of the blood vessels, accelerating the process of atherosclerosis and increasing the likelihood that a blood clot may develop. This could lead to a heart attack and/or stroke.

Sustained high blood pressure may eventually result in an enlarged and damaged heart (hypertrophy), which may lead to heart failure. Heart failure is the final common expression of a variety of cardiovascular disorders, including ischemic heart disease. It is characterized by an inability of the heart to pump enough blood to meet the body's needs and results in fatigue, reduced exercise capacity and poor survival. It is estimated that approximately 5,000,000 people in the United States suffer from heart failure, directly leading to 39,000 deaths per year and contributing to another 225,000 deaths per year.

A number of drug treatments have been proposed for the management of hypertension, heart failure, and other cardiovascular disorders. These include vasodilators to reduce the blood pressure and ease the workload of the heart, diuretics to reduce fluid overload, inhibitors and blocking agents of the body's neurohormonal responses, and other medicaments. Various surgical procedures have also been proposed for these maladies. For example, heart transplantation has been proposed for patients who suffer from severe, refractory heart failure. Alternatively, an implantable medical device such as a ventricular assist device (VAD) may be implanted in the chest to increase the pumping action of the heart. Alternatively, an intra-aortic balloon pump (IABP) may be used for maintaining heart function for short periods of time, but typically no longer than one month.

Although each of these approaches is beneficial in some ways, each of the therapies has its own disadvantages. For example, drug therapy is often incompletely effective. Drugs often have unwanted side effects and may need to be given in complex regimens. These and other factors contribute to poor patient compliance with medical therapy. Drug therapy may also be expensive, adding to the health care costs associated with these disorders.

2. Brief Description of the Background Art

It has been known for decades that the wall of the carotid sinus, a structure at the bifurcation of the common carotid arteries, contains stretch receptors (baroreceptors) that are sensitive to the blood pressure. These receptors send signals via the carotid sinus nerve to the brain, which in turn regulates the cardiovascular system to maintain normal blood pressure (the baroreflex), in part through modulation of the sympathetic and/or parasympathetic, collectively the autonomic, nervous system. Electrical stimulation of the carotid sinus nerve (baropacing) has previously been proposed to reduce blood pressure and the workload of the heart in the treatment of high blood pressure and angina.

Rau et al. (2001) Biological Psychology 57:179-201 describes animal and human experiments involving baroreceptor stimulation. U.S. Pat. Nos. 6,073,048 and 6,178,349, each having a common inventor with the present application, describe the stimulation of nerves to regulate the heart, vasculature, and other body systems. U.S. Pat. No. 6,522,926, assigned to the assignee of the present application, describes a number of systems and methods intended to activate baroreceptors in the carotid sinus and elsewhere in order to induce the baroreflex system. Numerous specific approaches are described, including the use of coil electrodes placed over the exterior of the carotid sinus near the carotid bifurcation. Nerve stimulation for other purposes is described in, for example, U.S. Pat. Nos. 6,292,695 B1 and 5,700,282. Publications which describe the existence of baroreceptors and/or related receptors in the venous vasculature and atria include Goldberger et al. (1999) *J. Neuro. Meth.* 91:109-114; Kostreva and Pontus (1993)*Am. J. Physiol.* 265:G15-G20; Coleridge et al. (1973) *Circ. Res.* 23:87-97; Mifflin and Kunze (1982) *Circ. Res.* 51:241-249; and Schaurte et al. (2000) *J. Cardiovasc Electrophysiol.* 11:64-69. U.S. Pat. No. 5,203,326 describes an anti-arrhythmia pacemaker. PCT patent application publication number WO 99/51286 describes a system for regulating blood flow to a portion of the vasculature to treat heart disease. The full texts and disclosures of all the references listed above (including the "related applications" earlier referenced above) are fully incorporated herein by reference in their entirety.

Cardiac resynchronization therapy (CRT) devices are known. Examples of CRT devices and methods are described in U.S. Pat. Nos. 6,768,923; 6,766,189; 6,748,272; 6,704,598; 6,701,186; and 6,666,826; the full disclosures of which are hereby incorporated by reference in their entirety.

An example of an implantable blood pressure measurement device that may be disposed about a blood vessel is disclosed in U.S. Pat. No. 6,106,477 to Miesel et al. An example of a subcutaneous ECG monitor is available from Medtronic under the trade name REVEAL ILR and is disclosed in PCT Publication No. WO 98/02209. Other examples are disclosed in U.S. Pat. Nos. 5,987,352 and 5,331,966. Examples of devices and methods for measuring absolute blood pressure utilizing an ambient pressure reference are disclosed in U.S. Pat. No. 5,810,735 to Halperin et al.; U.S. Pat. No. 5,904,708 to Goedeke; and PCT Publication No. WO 00/16686 to Brockway et al. The full texts and disclosures of all the references listed above are hereby incorporated fully by reference in their entirety.

SUMMARY OF THE INVENTION

To address the problems of hypertension, heart failure, other cardiovascular and non-cardiovascular disorders, nervous system and renal disorders, the present invention provides methods, devices, and systems for increasing the longevity of energy source (e.g., battery life) for activating at least one baroreflex system within a patient's body using a baroreflex activation device. Such activation, helps achieve effects that include reducing excessive blood pressure, autonomic nervous system activity, and neurohormonal activation. Such activation suggests to the brain an increase in blood pressure and the brain in turn regulates (e.g., decreases) the level of sympathetic nervous system and neurohormonal activation, and increases parasypathetic nervous system activation, thus reducing blood pressure and having a beneficial effect on the cardiovascular system and other body systems. As used herein, for convenience, the term "baroreceptor" will refer to collectively, receptors, including baroreceptors, mechanoreceptors, pressoreceptors, or any other arterial, venous, heart, or cardiopulmonary receptors which affect the blood pressure, nervous system activity, and neurohormonal activity in a manner analogous to baroreceptors in the arterial vasculature. The activation of the baroreflex system may also be affected by stimulating nerves which carry signals from such baroreceptors. As used herein, the term "baroreflex activation device" means a device that is located at or near a baroreceptor, so as to activate the baroreflex system within the patient's body. For the purposes of discussions, the present invention will be further explained referring to baroreceptors, but that is not intended to limit the scope of the present invention and applies to nerves (e.g., as referenced above). Furthermore, the present invention, although will be mainly discussed in reference to baroreflex activation systems, baroreflex devices, and implantable pulse generators in the context of such systems and devices; it is applicable to preservation of energy in other neurostimulators, where for example, the neurostimulator performance is not limited to delivery of power at a constant voltage in order to adequately activate such nerves or receptors (e.g., pacemakers where in order to provide adequate stimulation, it is necessary to operate at a constant voltage or other constant electrical output). It should be further appreciated by those skilled in the art that although the present invention is discussed and is of particular relevance to implantable pulse generators, it is also applicable to external pulse generators. Thus, the present invention and all embodiments described herein are applicable to pulse generators which are external (and not implantable) as well as those which are implantable. It should be further understood by those skilled in the art that the methods, devices, and systems according to the present invention are further applicable to modifying any one or more of the nervous system activity of the patient, autonomic nervous system activity of the patient, sympathetic/parasympathetic nervous system activity of the patient, or metabolic activity of the patient.

In an embodiment, a method for controlling an implantable pulse generator for activation of a nerve or receptor is provided. The method includes applying electrical power from the implantable pulse generator to the nerve or receptor. The energy level of the implantable pulse generator is monitored, while changing the operation of the implantable pulse generator to adjust the electrical power output of the implantable pulse generator while maintaining adequate nerve or receptor response. In an embodiment, the energy level is monitored by either or both monitoring the voltage and the current drain of the implantable pulse generator. In some embodiments, monitoring the energy level produces a signal when the energy level of the implantable pulse generator is at a first threshold energy level. The signal may also be generated prior to reaching the first energy threshold level. In some embodiments, the signal is produced when the implantable pulse generator energy level is about 0.25 Volts from the first threshold energy level. The monitoring, and the adjusting of the energy level of the energy source and the reduction in the consumption of the energy source is continued, as for example, in multiple steps, before the battery reaches its end of life. There may be more than one energy threshold level in some embodiments of the present invention, as for example, a second energy threshold level, which is indicative of a lower energy level than the first energy threshold level. The monitoring or adjusting may continue until the battery source runs out of life or its energy is replenished. In another embodiment, the energy level of the battery is calculated based on one or more parameters of the therapy.

In some embodiments, the activation of the nerve or receptor causes a baroreflex response in a patient. The activation of the baroreflex response may be by way of stimulating a baroreceptor or a nerve leading from a baroreceptor. In some embodiments, the implantable pulse generator changes its power output to further reduce energy consumption of the implantable pulse generator while maintaining adequate baroreflex response.

In an embodiment, a method for baroreflex activation is affected by applying a control signal to the baroreflex activation device, which in turn can apply one or more of different kinds of stimuli to one or more baroreceptors and/or nerve fibers that carry signals from the baroreceptors to the brain in the vicinity of the activation device. In an embodiment, the control signal that energizes the baroreflex activation device is an electrical signal.

In an embodiment, the electrical control signal is delivered to the baroreflex activation device by way of pulses generated by an implantable pulse generator (IPG) which is normally housed in a single bio-compatible container, such as metal container. Implantable pulse generators are powered by a battery, usually having a limited supply of energy, and housed within the container. However, although the discussion in further explaining the present invention is provided regarding non-replaceable batteries housed within an IPG, the present invention is applicable to both rechargeable batteries as well as non-replaceable batteries. The IPG, normally, further includes a pulse generator having a pulse generator circuitry, control systems, circuitry for controlling the electrical control signals, memory for storing data and therapy regimens for stimulation of the bareceptor, and a microprocessor for processing the signals and commands; all of which are normally included in the housing. The IPG is completely implanted under the skin of the patient in the pectoral region. The IPG in turn is connected by way of one or more electrical leads to the baroreflex activation device which includes one or more electrode assemblies, each assembly including one or more electrodes which may be placed adjacent a particular part of the human body, such as a baroreceptor (as broadly defined above). The one or more electrodes are attachable at a distal end of a corresponding lead, with the proximal end of the one or more leads connectable to a header of the implantable pulse generator.

In some methods embodying features of the present invention, the amount of electrical output provided to the baroreflex activation device by the IPG is controlled, to prolong the life of the battery.

In some embodiments, depending on the specific conditions of the patient in need of baroreflex therapy, the method includes establishing one or more therapy regimens. The duration of time the battery may provide the necessary electrical output to the baroreflex activation device by way of the pulse generator before the battery approaches its end of life/energy supply ("end of service" or "EOS"), is dependent on the amount of energy output from the battery required to apply the therapy regimen used.

It is desirable to change the implantable pulse generator including the battery, at a pre-elected time ("elective replacement" or "ER"), elected by the physician and the patient, prior to the end of service of the battery. Normally, a threshold battery energy level is representative of an indication for the elective replacement of the implantable pulse generator including the battery. By way of example, such indication of elective replacement, may be based on a pre-selected level of energy remaining in the battery, at which time, the physician and the patient prefer to replace the implantable pulse generator. If the implantable pulse generator is not replaced at the elective replacement time, it is, preferably, replaced at some point in time after the battery has reached the threshold energy but before its end of life/service.

In some embodiments, a method for controlling the energy output of a battery in an implantable pulse generator for activation of a baroreflex activation device, includes establishing a therapy regimen including a plurality of dose regimens for stimulating a baroreceptor of a patient. At least one dose regimen requires a lower power consumption than at least one other dose regimen. The energy level of the battery is monitored during the therapy. The method further includes applying electrical power output from the implantable pulse generator to the baroreflex activation device. The electrical output is responsive to at least one of the dose regimens. The dose regimen is changed at least once to lower electrical consumption of the battery when the battery energy falls below the threshold energy.

The energy level of the battery is monitored by either one or both of monitoring the voltage of the battery, and calculating the amount energy remaining in the battery. In an embodiment, when calculating the amount of energy remaining in the battery (e.g., energy level), at any given time, the energy consumed to-date is compared to the initial starting energy level of the battery. In some embodiments, when the implantable pulse generator is not replaced in time, such as before the EOS, the generation of electrical energy output by the battery is ceased in order to shut down the implantable pulse generator, and thus the baroreflex activation device, in a controlled and/or predictable manner. Additionally, the patient's and/or the system's information is saved, for example by the IPG's microprocessor, to prevent loss of data.

In an embodiment, the dose regimen may be changed by changing one or more characteristics of the pulses generated by the pulse generator circuitry within the implantable pulse generator, and which are responsive to the dose regimen. Such characteristics may include one or more of duty cycle, pulse amplitude, pulse width, pulse frequency, pulse separation, pulse waveform, pulse polarity, and pulse phase.

In an embodiment, the energy of the battery is monitored in multiple steps. As the battery energy is further decreased, the dose regimen may further be changed to further reduce the energy consumption of the battery, thus prolonging the life of the battery. During this reduction period, although the level of baroreflex activation may not be at the optimum level, it enables further treatment of the patient before the battery reaches its end of life/service. Thus, the method, device, and systems are still able to provide adequate stimulation to provide some level of therapy to the patient.

The energy level of the battery is monitored and a signal representative of the energy level of the battery is interpreted to implement the changing of the dose regimen to reduce the energy consumption of the battery, when the battery level falls below the threshold energy. The signal interpreter may be either or both, integral to the implantable pulse generator, as by way of example, the processor; and external to the implantable pulse generator. In the former case, the IPG may be programmed to respond and adjust the level of energy output from the battery without user intervention. In an embodiment, the user may still be informed that the signal has received, in order to take further appropriate action. In the latter case, the signal representative of the energy level of the battery is non-invasively communicated to a programming system, by way of example by telemetry. The external programming system interprets the signal and based on the energy level, enables the operator (e.g., the physician or the patient) to change the dose regimen by way of an external input device which communicates non-invasively with the implantable pulse generator. As indicated above, the monitoring of the energy level, and changing of the dose regimen accordingly, may be accomplished in multiple steps until the battery has reached its end of life and is depleted of energy. In some embodiments, multiple threshold levels may be used to further indicate the need for further reduction of consumption of the energy of the battery.

In an embodiment upon reaching the end of life/service of the battery, the therapy regimen is ceased. Any data, including, but not limited to patient information and system data, is stored in the memory of the implantable pulse generator for use by the physician.

In an embodiment, a baroreflex activation system for stimulating the baroreflex system of a patient includes an implantable pulse generator which includes a battery for providing electrical energy for use by the implantable pulse generator; and a detector for detecting/monitoring the energy level of the battery. The implantable pulse generator further includes a pulse generator for generating stimulation pulses to the baroreflex system of the patient. The pulse generator may have multiple modes of operation for delivery of the pulses with the modes being responsive to the energy level of the battery. The implantable pulse generator is further configured to at least once change to a mode requiring lower electrical consumption of the battery when the energy level of the battery falls below the threshold energy.

In an embodiment, the implantable pulse generator further includes a processor for controlling the operation of the pulse generator. The pulse generator may further include a memory system for storing information regarding the therapy regimen for stimulation of the baroreflex system of the patient. In an embodiment, the therapy regimen includes a plurality of dose regimens, wherein at least one dose regimen requires a lower power consumption than at least one other dose regimen. At least one mode requiring the lower power consumption is operational when the energy level of the battery has reached the energy threshold level.

In an embodiment, the activation system further includes at least one lead with its proximal end connectable to the implantable pulse generator. The at least one lead, at its distal end is connectable to an electrode assembly which is locatable proximate one or more baroreceptors of the patient.

In some embodiments, the activation system is further provided with a programmer system for non-invasively communicating with the implantable pulse generator.

In an embodiment, an implantable pulse generator for stimulating the baroreflex system of a patient, includes a battery for providing electrical energy for use by the implantable pulse generator, and a detector/monitor for monitoring the energy level of the battery. The implantable pulse generator further includes a pulse generator circuitry for generating stimulation pulses to the baroreflex system of the patient. The pulse generator may have multiple modes of operation for delivery of pulses, the modes being responsive to the energy level of the battery. The pulse generator may be further configured for changing at least once to a mode requiring lower electrical consumption of the battery when the energy level of the battery falls below a threshold energy level. The implantable pulse generator may further include a processor for controlling the mode of operation, with the mode of operation being at least once changed to lower electrical consumption of the battery when the battery energy falls below the threshold energy level.

In an embodiment, the implantable pulse generator further includes a memory system which is in communication with the processor and the battery. The memory system is configured for storing information regarding a therapy regimen. The therapy regimen includes a plurality of dose regimens for stimulating the baroreceptor system of the patient, with the at least one dose regimen requiring a lower power consumption than at least one other dose regimen. At least one of the dose regimens requiring the lower power consumption of the battery corresponds to the mode requiring the lower electrical consumption of the battery when the energy level of the battery falls below a threshold energy level.

In an embodiment, the implantable pulse generator is connectable to at least one electrical lead which is connectable to an electrode assembly locatable proximate one or more baroreceptors of the patient.

In some embodiments, the time interval between the elective replacement time and the end of services may range from about 5 to about 30 days, normally about fifteen (15) days based on a nominal programming condition. As used herein, the term "days" refers to a twenty-four hour time period. The time interval between the elective replacement time and the end of services, may further vary depending on the battery's initial energy and the therapy regimen (or regimens) used.

In some embodiments, establishing the amount of energy left within the battery includes measuring the battery's voltage and/or calculating the amount of energy that has been consumed at any given point in time. The voltage of the implantable pulse generator is determined by stimulation settings programmed by the user. The current or energy used is determined by the impedance of the attached lead and the voltage setting. The amount of energy consumed per date is measured or calculated based on the amount of pulses the implantable pulse generator has delivered at any given time based on the current parameter settings.

In another embodiment, the energy of the battery is monitored by calculating a replacement date based on the known energy of the battery at the beginning of its life, the parameters programmed into the device and the characteristics of the device itself. Changes made to any of the programmed parameters will result in an instantaneous adjustment of the replacement date.

It should be appreciated that methods and devices according to the present invention may be used alone or in combination with other therapy methods and devices to achieve separate, complementary, or synergistic effects. Examples of such other methods and devices include Cardiac Resynchronization Therapy (CRT); Cardiac Rhythm Management (CRM); anti-arrhythmia treatment as for example applied to the heart via a cardiovertor/defibrillator; drug delivery devices and systems; as well as diagnostic and/or monitoring modalities. The above devices and/or systems may be separate or integrated into a combination device in which the component therapies perform independently or in concert.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention. The drawings illustrate the specific embodiment where one or more baroreflex activation devices are positioned near baroreceptors. However, as can be appreciated, the invention is applicable to baroreflex activation devices that are positioned near nerve fibers that carry signals from the baroreceptor to the brain.

Anatomical Overview

Figure 1:
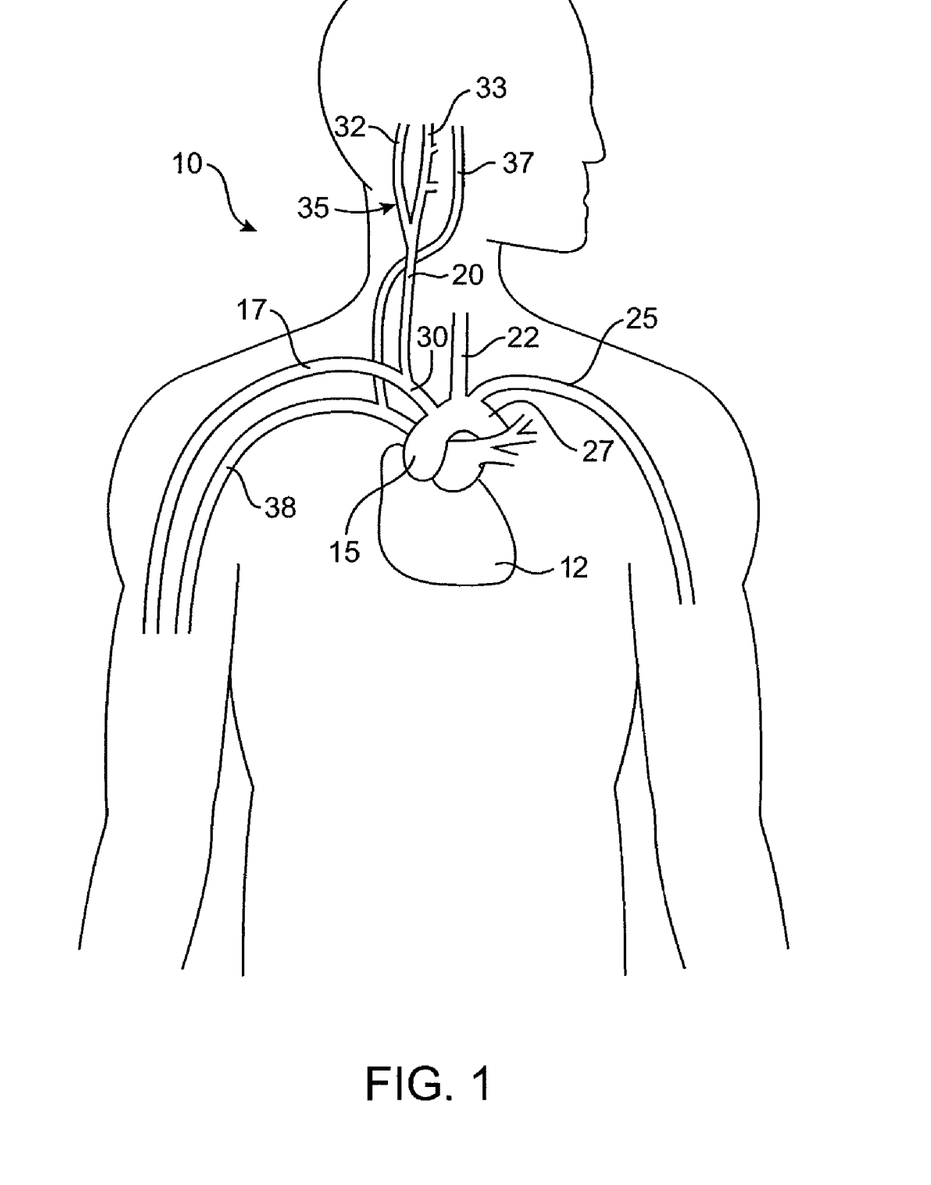
FIG. 1 is a schematic illustration of the chest and head regions of a human body showing the major arteries, veins, and associated anatomy.

Referring to FIG. 1, chest and head regions of a human body 10 including some of the major arteries and veins of the cardiovascular system are schematically shown. The left ventricle of a heart 12 pumps oxygenated blood up into the aortic arch 15. The right subclavian artery 17, the right common carotid artery 20, the left common carotid artery 22, and the left subclavian artery 25 branch off the aortic arch 15 proximal of the descending thoracic aorta 27. Although relatively short, a distinct vascular segment referred to as the brachiocephalic artery 30 connects the right subclavian artery 17 and the right common carotid artery 20 to the aortic arch 15. The right carotid artery 20 bifurcates into the right external carotid artery 32 and the right internal carotid artery 33 at the right carotid sinus 35. Although not shown, for purposes of clarity only, the left carotid artery 22 similarly bifurcates into the left external carotid artery and the left internal carotid artery at the left carotid sinus.

From the aortic arch 15, oxygenated blood flows into the carotid arteries 20/22 and the subclavian arteries 17/25. From the carotid arteries 20/22, oxygenated blood circulates through the head and cerebral vasculature and oxygen-depleted blood returns to the heart 12 by way of the jugular veins, of which only the right internal jugular vein 37 is shown for sake of clarity. From the subclavian arteries 17/25, oxygenated blood circulates through the upper peripheral vasculature and oxygen depleted blood returns to the heart by way of the subclavian veins, of which only the right subclavian vein 38 is shown, also for sake of clarity. The heart 12 pumps the oxygen depleted blood through the pulmonary system where it is re-oxygenated. The re-oxygenated blood returns to the heart 12 which pumps the re-oxygenated blood into the aortic arch as described above, and the cycle repeats.

Figure 2A:
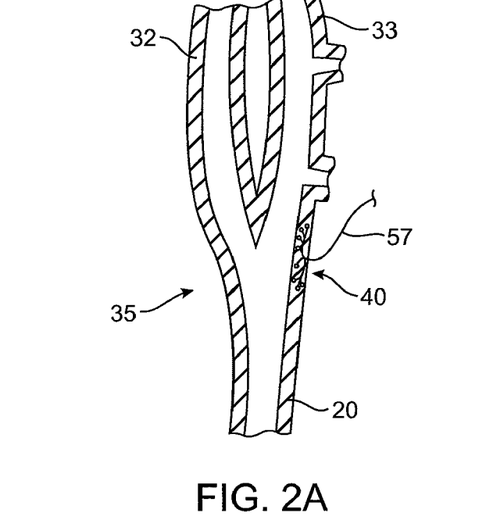
FIG. 2A is a cross-sectional schematic illustration of the carotid sinus and baroreceptors within the vascular wall.

FIG. 2A is a cross-sectional schematic illustration of the right carotid sinus 35 showing the presence of baroreceptors 40 within the vascular wall of the right common carotid artery 20 near the right carotid sinus 35. Baroreceptors are also present, for example, within the arterial walls of the aortic arch 15, the left common carotid artery 22 (near the left carotid sinus), subclavian arteries 17/25, and brachiocephalic artery 30. Baroreceptors 40 are a type of stretch receptor used by the body to sense blood pressure, and exists in both arterial and venous structures. An increase in blood pressure causes the vascular wall to stretch, and a decrease in blood pressure causes the vascular wall to return to its original size. Such a cycle is repeated with each beat of the heart. Because baroreceptors 40 are located within the vascular wall, they are able to sense deformation of the adjacent tissue, which is indicative of a change in blood pressure. As used herein, the term "baroreceptors" is used to refer to baroreceptors in arterial vasculation, as well as mechanoreceptors, pressoreceptors, or any other venous heart, or cardiopulmonary receptors which affect the blood pressure, nervous system activity, and neurohormonal activity in a manner analogous to baroreceptors in the arterial vasculation. For convenience, all such venous receptors (and/or nerves carrying signals from such receptors) whether, in arteries or veins, will be referred to collectively herein as "baroreceptors." Thus, for discussion purposes, it will be assumed that baroreceptors 40 are connected to the brain 55 via the nervous system 60.

Figure 2B:
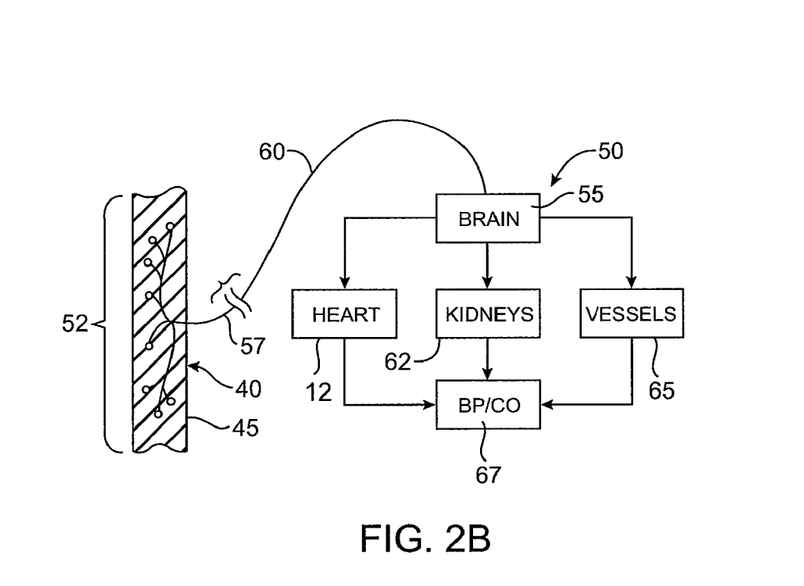
FIG. 2B is a schematic illustration of baroreceptors within a vascular wall, and a schematic flow chart of the baroreflex system.

FIG. 2B is a schematic illustration of baroreceptors 40 within a generic vascular wall 45 and showing the interaction with the baroreflex system, denoted schematically as 50. The baroreceptors 40 located in the right carotid sinus 35, the left carotid sinus, and the aortic arch 15 play the most significant role in sensing blood pressure that affects the baroreflex system 50, which is now described in more detail. Specifically, baroreceptors 40 are profusely distributed within the vascular walls 45 of the major arteries discussed previously, and generally form an arbor 52. Baroreceptor arbor 52 comprises a plurality of baroreceptors 40, each of which transmits baroreceptor signals to the brain 55 via a nerve 57. Baroreceptors 40 are so profusely distributed and arborized within the vascular wall 45 that discrete baroreceptor arbors 52 are not readily discernable. To this end, those skilled in the art will appreciate that baroreceptors 40 shown in FIG. 2B are primarily schematic for purposes of illustration and discussion.

Baroreceptor signals are used to activate a number of body systems which collectively may be referred to as baroreflex system 50. Baroreceptors 40 are connected to the brain 55 via the nervous system 60. Thus, the brain 55 is able to detect changes in blood pressure, which is indicative of cardiac output. If cardiac output is insufficient to meet demand (i.e., the heart 12 is unable to pump sufficient blood), baroreflex system 50 activates a number of body systems, including the heart 12, kidneys 62, vessels 65, and other organs/tissues. Such activation of the baroreflex system 50 generally corresponds to an increase in neurohormonal activity. Specifically, baroreflex system 50 initiates a neurohormonal sequence that signals the heart 12 to increase the heart rate and increase contraction force in order to increase cardiac output, signals the kidneys 62 to increase blood volume by retaining sodium and water, and signals the vessels 65 to constrict to elevate blood pressure. The cardiac, renal and vascular responses increase blood pressure and cardiac output (denoted schematically at 67), and thus increase the workload of the heart 12. In a patient with heart failure, this further accelerates myocardial damage and exacerbates the heart failure state.

System Overview

To address the problems of hypertension, heart failure, other cardiovascular disorders, nervous system and renal disorders, the present invention provides methods, devices, and systems by which baroreflex system 50 is activated to reduce excessive blood pressure, autonomic nervous system activity, and neurohormonal activation. Such activation systems signal to the brain 55 the increase in blood pressure and the brain in turn regulates (e.g., decreases) the level of sympathetic nervous system and neurohormonal activation, and increases parasympathetic nervous system activation, thus reducing blood pressure and having a beneficial effect on the cardiovascular system and other body systems.

Figure 3:
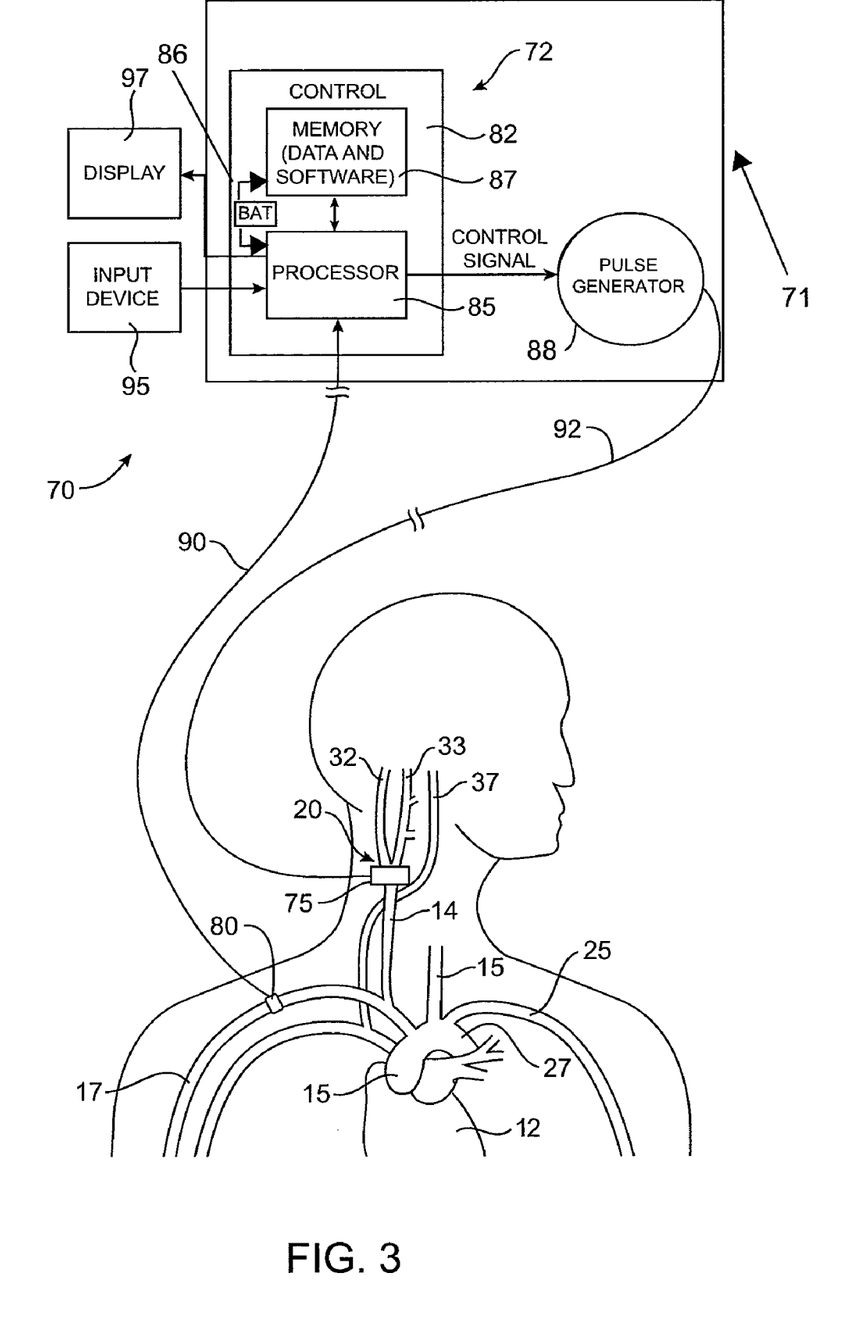
FIG. 3 is a schematic illustration of a baroreflex activation system applied to a human subject according to an embodiment of the present invention.

FIG. 3 is a schematic illustration of a baroreflex activation system 70 applied to a human subject according to an embodiment of the present invention. The human subject may be the person shown in FIG. 1, and corresponding reference numbers are used. In brief, baroreflex activation system 70 includes an implantable pulse generator 71 including a control system 72, a baroreflex activation device 75, and an optional sensor 80, which generally operate in the following manner. Sensor 80 optionally senses and/or monitors a parameter (e.g., cardiovascular function) indicative of the need to modify the baroreflex system and generates a signal indicative of the parameter. In some embodiments (not shown), sensor 80 may be incorporated into the structure of baroreflex activation device 75.

Control system 72 generates a control signal which activates a pulse generator 88 for generating pulses that activate, deactivate, or otherwise modulate baroreflex activation device 75. Typically, activation of baroreflex activation device 75 results in activation of baroreceptors 40 and/or nerve fibers that carry signals from the baroreceptor to the brain. Alternatively, deactivation or modulation of baroreflex activation device 75 may cause or modify activation of baroreceptors 40 and/or nerve fibers (such as carotid sinus nerve fibers) that carry signals from the baroreceptor to the brain. Control system 72 may generate the control signal according to a predetermined schedule or in response to human action.

For embodiments using optional sensor 80, the control system can generate the control signal as a function of the received sensor signal. This could be independent of a predetermined schedule, or as an adjunct to the schedule. For example, if sensor 80 were to detect a parameter indicative of the need to modify the baroreflex system activity (e.g., excessive blood pressure), control system 72 would cause the control signal to modulate (e.g., activate and/or increase) baroreflex activation device 75, thereby inducing a signal from baroreceptor 40 and/or nerve fibers near the baroreceptor to the brain that is perceived by the brain 55 to be apparent excessive blood pressure. When sensor 80 detects a parameter indicative of normal body function (e.g., normal blood pressure), control system 72 would cause the control signal to modulate (e.g., deactivate and/or decrease) baroreflex activation device 75. The sensor and control system may also be used to control timing of the delivery of the therapy, for example being R-wave triggered, and/or they may also dictate the timing or intensity of the therapy relative to a respiratory cycle. The sensor may also determine the sidedness of the therapy (for example, in the presence of arterial fibrillation versus Normal Sinus Rhythm).

As shown, control system 72 includes a control block 82 comprising a processor 85, and a memory 87, for controlling pulse generation by the pulse generator 88. A battery 86 supplies energy to the control block 82 and the pulse generator 88. Control system 72 is connected to sensor 80 by way of a sensor cable 90. The implantable pulse generator may be also connected to baroreflex activation device 75 by way of a control cable 92. Thus, control system 72 receives a sensor signal from sensor 80 by way of sensor cable 90, and transmits a control signal to the pulse generator 88, and thereby the baroreflex activation device 75, by way of control cable 92. The implantable pulse generator is also typically provided with an input device 95 and an output device or display 97 (collectively, "Programmer System"). The programmer system is typically in communication with the implantable pulse generator in a non-invasive manner, as for example by telemetry.

Figure 4:
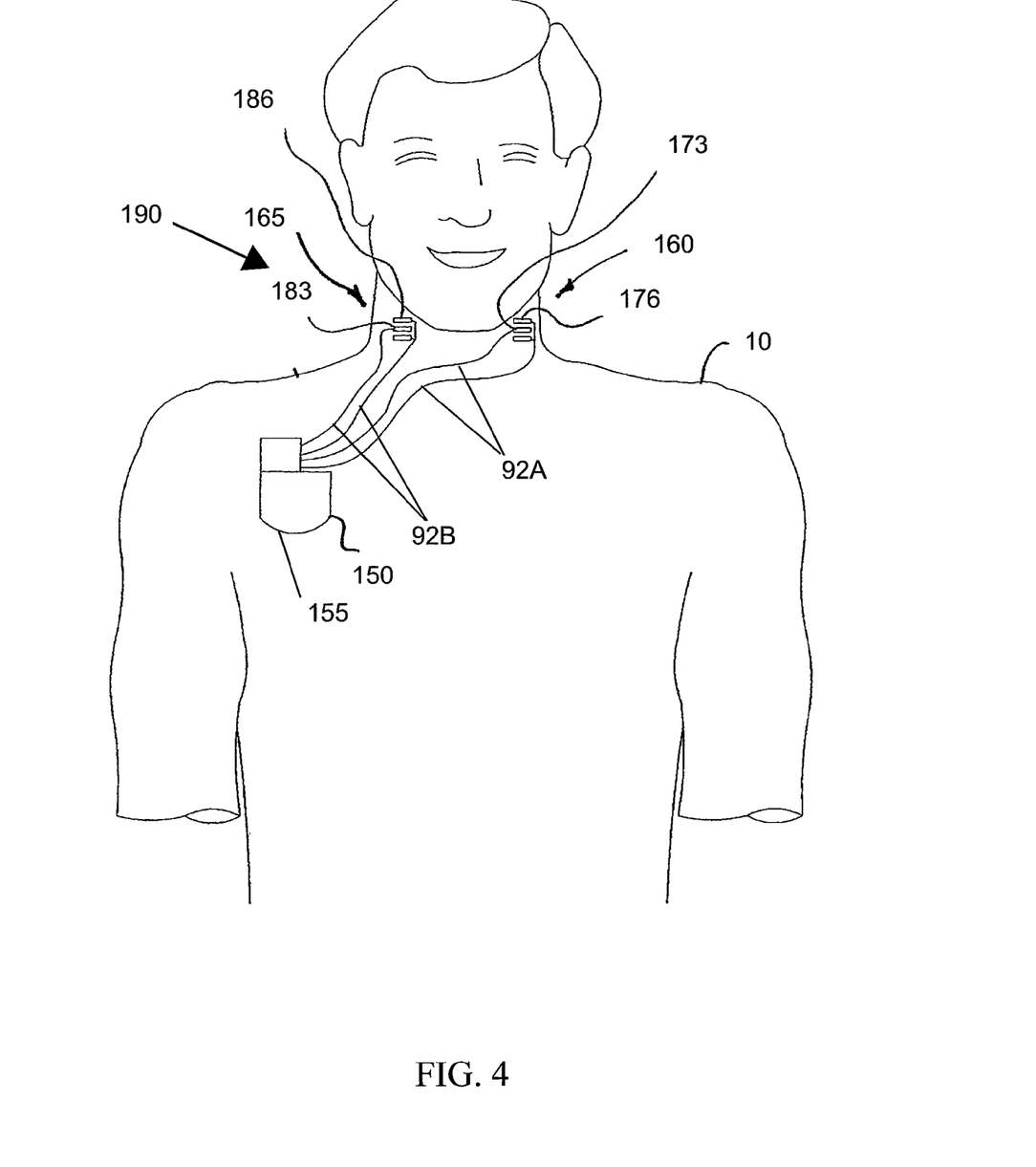
FIG. 4 is a schematic illustration of an exemplary diagram representative of a process for extension of a battery life supplying power to a baroreflex activation device, employing features of the present invention.

System components 71/75/80 may be directly linked via cables 90/92 or by indirect means such as RF signal transceivers, ultrasonic transceivers, or galvanic couplings. Examples of such indirect interconnection devices are disclosed in U.S. Pat. No. 4,987,897 to Funke and U.S. Pat. No. 5,113,859 to Funke, the entire disclosures of which are incorporated herein by reference. The pulse generator 88 provides the desired pulses for activation of the baroreflex activation device 75. The pulse generator 88 may comprise a power amplifier or the like and cable 92 may comprise electrical lead(s). The electrode structure (electrode assemblies 160 and 165 as shown in FIG. 4) of the baroreflex activation device 75 receives electrical signals from the pulse generator 88 of the implantable pulse generator 71 by way of electrical lead 92 (e.g., 92A and 92B as shown in FIG. 4). Various electrode designs are described in co-pending commonly assigned application Ser. No. 10/402,911 as well as related applications previously referenced above and incorporated herein by reference in their entirety. As described above, and as further shown in reference to FIG. 4, the implantable pulse generator is implanted in the pectoral region of the patient 10, with leads 70 providing electrical communication between the implantable pulse generator and the one or more electrode assemblies of the baroreflex activation device.

As further shown in detail in FIG. 4, embodying features of the present invention, an implantable pulse generator 155 including the control system 72, the battery 86, and the pulse generator 88, are integrated and located in a housing 150 within the pectoral region of patient 10. The implantable pulse generator 155 is connectable to first and second electrode assemblies 160 and 165 by way of leads 92A and 92B which are connected at a proximal end to the implantable pulse generator 155 and at a distal end to the electrode assemblies of the baroreflex activation device. Each electrode assembly, respectively, includes first and second electrodes; 173 and 176, and 183 and 186; together forming the baroreflex activation device 190.

Methods of Controlling the Energy Output of the Battery

The stimulus regimen governed by implantable pulse generator 71/155 may be selected to promote long term efficacy. The stimulus regimen may be selected to activate, deactivate or otherwise modulate baroreflex activation device 75 (or 190) in such a way that therapeutic efficacy is maintained for months, preferably for years. The therapy regimen and the methods embodying features of the present invention control and prolong the life of the battery, providing the source of electrical energy for applying power to the baroreflex activation device 75/190, to enable a controlled cessation of therapy to a patient in the event that the implantable pulse generator is not replaced in the desired time frame. The therapy regimen chosen for a particular patient includes providing electrical stimuli through the implantable pulse generator 155 to the baroreflex activation device. The therapy regimen may include one or more dose regimens usable within the therapy regimen.

In some embodiments, the duration of time the battery may provide the necessary electrical output to the baroreflex activation device by way of the pulse generator 88 before the battery approaches its end of time/energy supply ("end of service" or "EOS"), is dependent on the battery's energy level and the therapy regimen used. Upon the occurrence of the EOS, the battery will be depleted of energy.

The method may include establishing an elective indicator representative of an indication to the physician and/or the patient that the time to replace the battery is forthcoming ("elective replacement indicator" or "ERI"). The ERI may be based on a pre-selected battery energy threshold, chosen based on the battery's initial energy and the one or more therapy regimens used to treat the patient. The ERI may be calculated and input into the baroreflex activation system (e.g., the memory) or may be calculated by the baroreflex activation system itself (e.g., the electronics, such as the microprocessors of the baroreflex activation system including the IPG). In some embodiments, the time interval between the elective replacement time and the end of services may range from about 5 to about 30 days, normally about fifteen (15) days based on a nominal programming condition. As used herein, the term "days" refers to a twenty-four hour time period.

There may be instances of delay between the elective time for replacement and the time the battery is replaced before the occurrence of the EOS. Examples of such delays include, but are not limited to, instances where the patient requires higher output settings to reach the desired therapy results, or when the battery is not replaced upon the occurrence of the elective time for replacement (or the energy threshold level of the battery.

In an embodiment, a method for extending the battery life after the elective time for replacement and before the EOS, includes controlling the amount of electrical consumption by the implantable pulse generator during the time between the elective replacement indicator and the end of service. The extending of the battery's life, in some embodiments, includes changing of the one or more dose regimens such that the amount of energy delivered from the IPG to the baroreflex activation device, is reduced. This extending of battery life, enables the physician and the patient to schedule a suitable replacement time of the battery.

In some embodiments, the amount of energy available in the battery, at any given time, is established by measuring and/or monitoring the amount of energy remaining ("remaining energy") within the battery. The measurement/monitoring may be accomplished by, for example, a microprocessor which is housed along with the pulse generator as part of the overall baroreflex activation system in the biocompatible container (which is normally housed under the skin in the pectoral region). In some embodiments, establishing the amount of energy remaining within the battery includes measuring the battery's voltage and/or calculating the amount of energy that has been consumed up to any given point in time as compared to the starting level of energy. The voltage of the implantable pulse generator is determined by stimulation settings programmed by the user. The current or energy used is determined by the impedance of the attached lead and the voltage setting. The amount of energy consumed per date is measured or calculated based on the amount of pulses the implantable pulse generator delivers in a day given the current parameter settings.

In other embodiments, the amount of energy available in the battery is established by determining the impedance of the lead coupled to the baroreflex device and combining that value with the programmed therapy parameters to determine a periodic (such as daily) energy consumption. The periodic consumption is compared to the known initial total energy of the battery to determine the battery lifespan. Additional information on such an embodiment can be found in U.S. Provisional Application No. 60/951,114, entitled "Elective Replacement Indicator Based On Pulse Count," the disclosure of which is hereby incorporated by reference in its entirety.

In some embodiments, the intermediate indicator is compared with the elective replacement indicator, and provides a first intermediate value which may be equal to, less than, or greater than the elective replacement indicator.

In some embodiments, the energy consumption of the battery may be changed by changing the voltage, current, signal duration and/or frequency of the pulse generator. In some embodiments, pulses delivered by the pulse generator to the baroreflex activation device and the electrical power applied to the baroreflex activation device can be varied by controlling one or more of pulse characteristics which are responsive to at least one of the dose regimens. The pulses are normally narrow pulses, and the electrical power output applied to the baroreflex activation device by the IPG for stimulating the baroreceptor system of the patient may be varied by controlling, independently, one or more of the pulse characteristics generated by the pulse generator. Such pulse characteristics include, but are not limited to, amplitude, pulse width (or duration), pulse frequency (or inversely, the interval between the starts of successive pulses), pulse waveform (e.g., square, triangular, sinusoidal), pulse polarity (for bipolar electrodes), and pulse phase (e.g., monophasic, and multiphasic including biphasic), and duty cycle. Such reduction of the parameters of the pulse characteristic may be effectuated in multiple steps. As the battery's energy is further reduced after reaching the battery and as it gets closer to the EOS, the above parameters, independently, may be further reduced to prolong the complete cessation of therapy. In some embodiments, although this reduction in the parameters, may lead to less than optimal blood pressure reduction (e.g., as less power output is generated by the IPG), it extends the time of at least partial blood pressure reduction until the pulse generator is replaced.

In some embodiments, when the IPG (including the battery) is not replaced in time, such as before the EOS, the generation of electrical energy output by the battery is ceased in order to shut down the implantable pulse generator and/or the baroreflex activation system (including the IPG), in a controlled and/or predictable manner. Additionally, the patient's and/or the system's information is saved, for example by the baroreflex activation system's microprocessor, to preserve any patient or system data and prevent loss of information.

Figure 5:
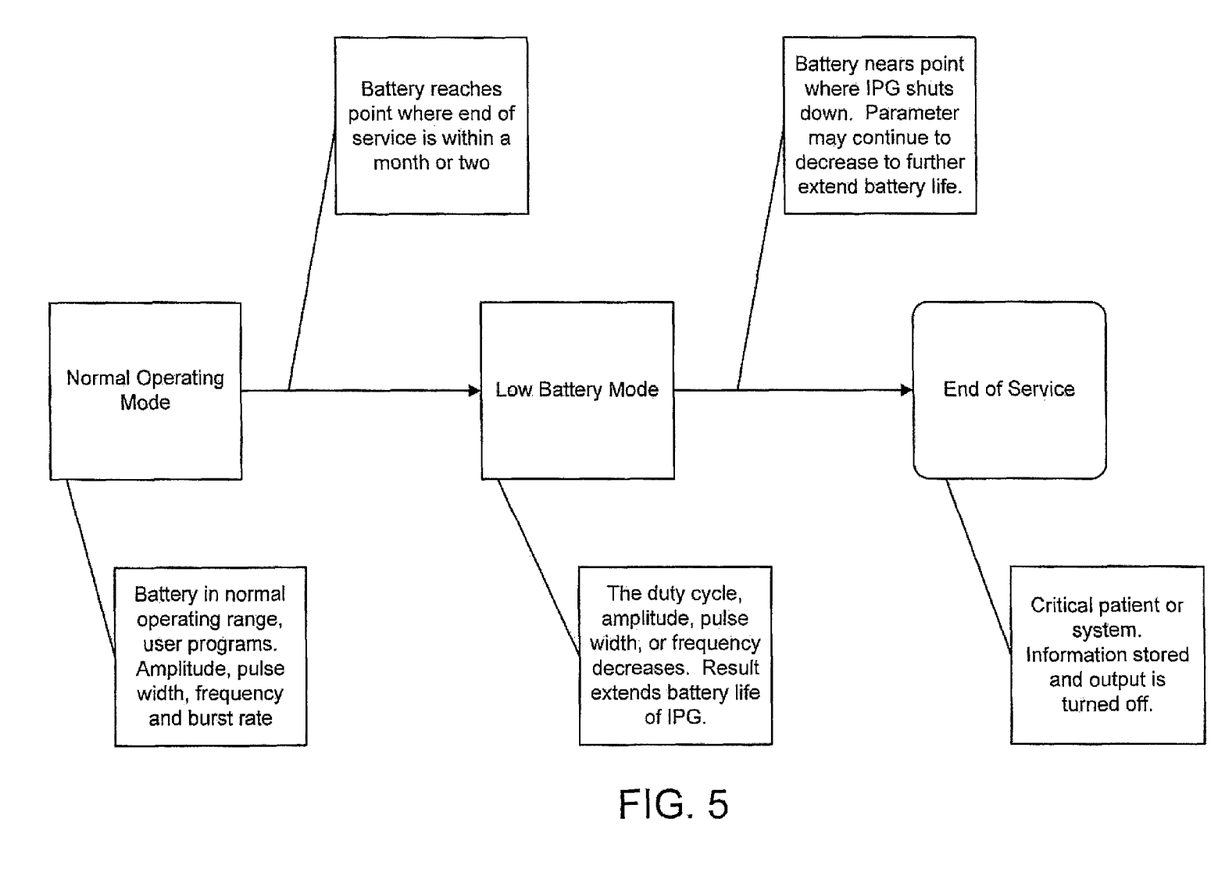
FIG. 5 is schematic representation of an exemplary baroreflex activation system including a transcutaneously implanted internal pulse generator and associated electrodes of a baroreflex activation device, embodying features of the present invention.

The above method, may further be described in relation to FIG. 5. The IPG begins its operation in the normal operating mode which is based, at least in part on the therapy regimen selected by the physician, and effectuated by the setting of the dose regimens within the therapy regimen. The battery in normal operating conditions is programmed to deliver electrical energy to the pulse generator by programming pulse characteristics which are responsive to at least one of the dose regimens. The microprocessor within the IPG monitors the energy level of the battery within the IPG (e.g., by way of measuring the battery's voltage or calculating the energy that has been consumed to-date) and once it detects that it has reached a pre-selected time from the EOS (e.g., 1 to 2 months), it automatically begins operation in the low battery mode to conserve energy. The low battery mode may be achieved by reducing any one or more of the pulse characteristics delivered by the pulse generator such as amplitude, pulse width, and pulse frequency. To further prolong the battery's life, the pulse generator may reduce the responsive pulse characteristics in one or more steps in order to further extend the longevity of the battery as it gets closer to the end of service. Although this may lead to less than optimal blood pressure reduction, it would extend the time of at least partial blood pressure reduction until the IPG (including the battery) is replaced. The information regarding the patient and the applied therapy is stored in the IPG's memory to prevent data loss, even in the event of complete shut down before the IPG is replaced in time.

Representative Baroreflex Activation Devices and Electrode Assemblies

Baroreflex activation device 75 may directly activate one or more baroreceptors 40 by changing the electrical potential across baroreceptors 40. It is also possible that changing the electrical potential might activate nerve fibers, or might indirectly change the thermal or chemical potential across the tissue surrounding baroreceptors 40 and/or otherwise may cause the surrounding tissue to stretch or otherwise deform, thus mechanically activating baroreceptors 40 and/or nerve fibers that carry signals from the baroreceptor to the brain. Thus, baroreflex activation device 75 activates baroreceptors 40 and/or nerve fibers that carry signals from the baroreceptor to the brain electrically, optionally in combination with mechanical, thermal, chemical, biological or other co-activation. Thus, when implantable pulse generator generates a control signal to modulate (e.g., activate) baroreflex activation device 75, this induces a signal from baroreceptor 40 and/or nerve fibers that carry signals from the baroreceptor to the brain that presumably are perceived by the brain 55 to be apparent excessive blood pressure, and the baroreflex system operates to lower the blood pressure. However, in the present invention, it is generally contemplated that the control signal that energizes baroreflex activation device 75 will be an electrical signal. The particular design of suitable electrodes are described in the referenced patents and applications, the full disclosures of which are hereby incorporated by reference. However, it should be appreciated that the methods and devices of the present invention may be used with any number of electrodes and configurations, as for example a tripolar electrode, a bipolar electrode, or a monopolar electrode (e.g., an electrode set including an active electrode and a dispersive electrode). For further details of exemplary electrodes useful in the practice of the present invention, reference may be made to U.S. Pat. Nos. 6,522,926; 6,616,624; 6,985,774; 7,158,832; and 6,850,801; and U.S. patent application Ser. Nos. 10/284,063, filed Oct. 29, 2002; 10/453,678, filed Jun. 2, 2003; 10/818,738, filed Apr. 5, 2004; 60/584,730, filed Jun. 30, 2004; 10/402,911, filed Mar. 27, 2003 (e.g., FIG. 27); 10/402,393, filed Mar. 27, 2003; 10/958,694, filed Oct. 4, 2004; and 60/882,478, filed Dec. 28, 2006, the full disclosures of all of which were previously incorporated by reference in their entirety.

Baroreflex activation device 75 is suitable for implantation, and is preferably implanted using a minimally invasive percutaneous transluminal approach and/or a minimally invasive surgical approach. Baroreflex activation device 75 may be positioned anywhere that baroreceptors 40 affecting baroreflex system 50 are numerous, such as in the heart 12, in the aortic arch 15, in the common carotid arteries 20/22 near the carotid sinus 35, in the subclavian arteries 17/25, in the brachiocephalic artery 30, in the femoral and/or iliac arteries (not shown), in the veins (not shown), or in the cardiopulmonary region (not shown). Baroreflex activation device 75 may be implanted such that it is positioned adjacent baroreceptors 40 and/or nerve fibers that carry signals from the baroreceptor to the brain. The implantable pulse generator is normally planted under the skin in the pectoral region of the patient's body.

For purposes of illustration only, the present invention is described with reference to baroreflex activation device 75 positioned near the carotid sinus 35. Furthermore, for clarity, FIG. 3 shows a single baroreflex activation device 75. However, it is believed that advantages can be achieved by providing two or more baroreflex activation devices, and energizing them in a synchronous, sequential, or alternating manner. For example, similar devices could be positioned in both carotid sinus regions (or other regions), and driven alternately.

Control System

Memory 87 may contain data related to the sensor signal, the control signal, the battery's energy level, therapy regimens, and/or values and commands provided by the optional input device 95. Memory 87 may also include software containing one or more algorithms defining one or more functions or relationships between the control signal and the sensor signal. The algorithm may dictate activation or deactivation control signals depending on the sensor signal or a mathematical derivative thereof. The algorithm may dictate an activation or deactivation control signal when the sensor signal falls below a lower predetermined threshold value, rises above an upper predetermined threshold value, or when the sensor signal indicates a specific physiologic event. The algorithm may dynamically alter the threshold value as determined by the sensor input values. Similarly, the memory 87, may include information and algorithms (as for example, described in relation to FIG. 5) relating to the battery 86, and the control of its energy output to prolong the life of the battery.

The implantable pulse generator may operate as a closed loop utilizing feedback from sensor 80, or other sensors, such as heart rate sensors which may be incorporated on the electrode assembly, or as an open loop utilizing reprogramming commands received by input device 95. The closed loop operation of the implantable pulse generator, preferably, utilizes some feedback from sensor 80, but may also operate in an open loop mode without feedback. Programming commands received by input device 95 may directly influence the control signal, the output activation parameters, or may alter the software and related algorithms contained in memory 87. The treating physician and/or patient may provide commands to input device 95. Display 97 may be used to view the sensor signal, battery energy level, estimated end of life/service time, control signal, and/or the software/data contained in memory 87. The communication between the input device and the display device may be without a physical connection, as for example telemetry devices.

The control signal generated by control system 72 to activate generation of pulses by the pulse generator 88 may be continuous, may provide for periodic, alternating, episodic pulses, or a combination thereof, as dictated by an algorithm contained in memory 87. In an embodiment, the generated pulses are further dependent on the energy level of the battery system and the algorithms contained in memory 87 to prolong the battery life. Continuous pulses include a constant pulse, a constant train of pulses, a triggered pulse, and a triggered train of pulses. Examples of periodic pulses include each of the continuous pulses described above which have a designated start time (e.g., beginning of each period as designated by minutes, hours, or days in combinations of) and a designated duration (e.g., seconds, minutes, hours, or days in combinations of). Examples of alternating pulses include each of the continuous pulses as described above which alternate between the right and left output channels. Examples of episodic pulses include each of the continuous pulses described above which are triggered by an episode (e.g., activation by the physician/patient, an increase/decrease in blood pressure above a certain threshold, heart rate above/below certain levels, respiration, etc.).

Representative Sensors

Now referring back to FIG. 3, while sensor 80, is optional, and embodiments of the invention can operate without using such a sensor, the sensor is a useful feature, and several representative types will be discussed. Sensor 80 may comprise any suitable device that measures or monitors a parameter indicative of the need to modify the activity of the baroreflex system. For example, sensor 80 may comprise a physiologic transducer or gauge that measures ECG, blood pressure (systolic, diastolic, average or pulse pressure), blood volumetric flow rate, blood flow velocity, respiration, blood pH, oxygen or carbon dioxide content, mixed venous oxygen saturation ($SVO_2$), vasoactivity, nerve activity, tissue activity, or tissue or blood composition. Examples of suitable transducers or gauges for sensor 80 include ECG electrodes, a piezoelectric pressure transducer, an ultrasonic flow velocity transducer, an ultrasonic volumetric flow rate transducer, a thermodilution flow velocity transducer, a capacitive pressure transducer, an impedance sensor, a membrane pH electrode, an optical detector ($SVO_2$) or a strain gauge. Although only one sensor 80 is shown, multiple sensors 80 of the same or different type at the same or different locations may be utilized.

An example of an implantable blood pressure measurement device that may be disposed about a blood vessel is disclosed in U.S. Pat. No. 6,106,477 to Miesel et al. An example of a subcutaneous ECG monitor is available from Medtronic under the trade name REVEAL ILR and is disclosed in PCT Publication No. WO 98/02209. Other examples are disclosed in U.S. Pat. Nos. 5,987,352 and 5,331,966. Examples of devices and methods for measuring absolute blood pressure utilizing an ambient pressure reference are disclosed in U.S. Pat. No. 5,810,735 to Halperin et al., U.S. Pat. No. 5,904,708 to Goedeke, and PCT Publication No. WO 00/16686 to Brockway et al. Sensor 80 described herein may take the form of any of these devices or other devices that generally serve the same purpose. The full disclosures of all of the above were previously incorporated by reference in their entirety.

Sensor 80 is preferably positioned in a chamber of the heart 12, or in/on a major artery such as the aortic arch 15, a common carotid artery 20/22, a subclavian artery 17/25 or the brachiocephalic artery 30, such that the parameter of interest may be readily ascertained. Sensor 80 may be disposed inside the body such as in or on an artery, a vein or a nerve (e.g., vagus nerve), or disposed outside the body, depending on the type of transducer or gauge utilized. Sensor 80 may be separate from baroreflex activation device 75 or combined therewith. For purposes of illustration only, sensor 80 is shown positioned on the right subclavian artery 17.

Although the above description provides a complete and accurate representation of the invention, the present invention may be manifested in a variety of forms other than the specific embodiments described and contemplated herein. Accordingly, departures in form and detail may be made without departing from the scope and spirit of the present invention as described in the appended claims.

What is claimed is:

1. A method of controlling an implantable pulse generator for baroreflex activation, comprising:
    applying electrical power from the pulse generator to a nerve or a receptor;
    monitoring the energy level of the pulse generator, including producing a signal representative of the energy level of the pulse generator in response to the energy level of the pulse generator reaching a first threshold energy level;
    changing the operation of the pulse generator to adjust the electrical power output of the pulse generator while maintaining adequate physiological response, comprising reducing energy consumption of the pulse generator in response to the signal representative of the energy level of the pulse generator while maintaining adequate baroreflex response; and
    monitoring the energy level of the pulse generator until the energy level reaches a second threshold level and generating a signal representative of the energy level of the pulse generator.

2. The method of claim 1, further comprising changing the power output of the pulse generator in response to the signal representative of the energy level of the pulse generator to further reduce energy consumption of the pulse generator while maintaining adequate baroreflex response.

3. A method of controlling the energy output of a battery in an implantable pulse generator for activation of a baroreflex activation device, the method comprising:
    establishing a therapy regimen including a plurality of dose regimens for stimulating a baroreflex of a patient, wherein at least one dose regimen requires a lower power consumption than at least one other dose regimen;
    monitoring the energy level of the battery;
    applying electrical power output from the implantable pulse generator to the baroreflex activation device, the electrical output being responsive to at least one of the dose regimens;
    changing the dose regimen at least once to lower electrical consumption of the battery when the battery energy falls below a threshold energy level; and
    alerting the patient and/or the healthcare provider when the battery energy falls below the threshold energy level.

* * * * *